(12) United States Patent
Colantonio

(10) Patent No.: US 9,682,227 B2
(45) Date of Patent: Jun. 20, 2017

(54) LEAD COUPLER FOR MULTIPLE NEUROLOGICAL STIMULATION LEADS

(71) Applicant: Anthony J. Colantonio, Meadville, PA (US)

(72) Inventor: Anthony J. Colantonio, Meadville, PA (US)

( * ) Notice: Subject to any disclaimer, the term of this patent is extended or adjusted under 35 U.S.C. 154(b) by 13 days.

(21) Appl. No.: 14/348,636

(22) PCT Filed: Oct. 9, 2012

(86) PCT No.: PCT/US2012/059289
§ 371 (c)(1),
(2) Date: Mar. 31, 2014

(87) PCT Pub. No.: WO2013/052962
PCT Pub. Date: Apr. 11, 2013

(65) Prior Publication Data
US 2014/0236259 A1    Aug. 21, 2014

Related U.S. Application Data

(60) Provisional application No. 61/627,166, filed on Oct. 7, 2011.

(51) Int. Cl.
*A61N 1/00*    (2006.01)
*A61N 1/05*    (2006.01)

(52) U.S. Cl.
CPC ............. *A61N 1/0551* (2013.01); *A61N 1/05* (2013.01); *A61N 2001/058* (2013.01)

(58) Field of Classification Search
CPC ............................. A61N 1/0551; A61N 1/375
USPC ......................................................... 607/116
See application file for complete search history.

(56) References Cited

U.S. PATENT DOCUMENTS

2005/0203599 A1*  9/2005  Garabedian .......... A61N 1/0551
                                                                 607/116
2008/0281381 A1* 11/2008  Gerber ............... A61N 1/36514
                                                                  607/62
2011/0009933 A1*  1/2011  Barker ................. A61N 1/0551
                                                                 607/116

* cited by examiner

*Primary Examiner* — Amanda Patton
*Assistant Examiner* — Philip C Edwards
(74) *Attorney, Agent, or Firm* — Carothers & Carother

(57) ABSTRACT

An implantable neurological stimulation lead assembly (10) having multiple elongated stimulation leads coupled together in parallel with a lead coupler (13) for delivering electrical impulses to subcutaneous tissue for treatment. The lead coupler (13) includes a set of interconnected expandable elastic collars (15), one collar for each lead (11,12), whereby the collars (15) respectively receive and retain the leads (11,12) with an elastic constraint in a predetermined side by side array. The set of interconnected lead coupler collars (15) are interconnected with a releasable connection (23) whereby the lead assembly (10) may be configured as a single or multiple lead assembly.

3 Claims, 4 Drawing Sheets

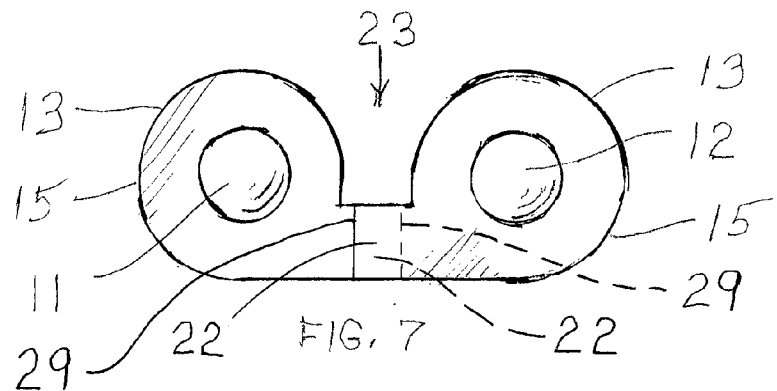
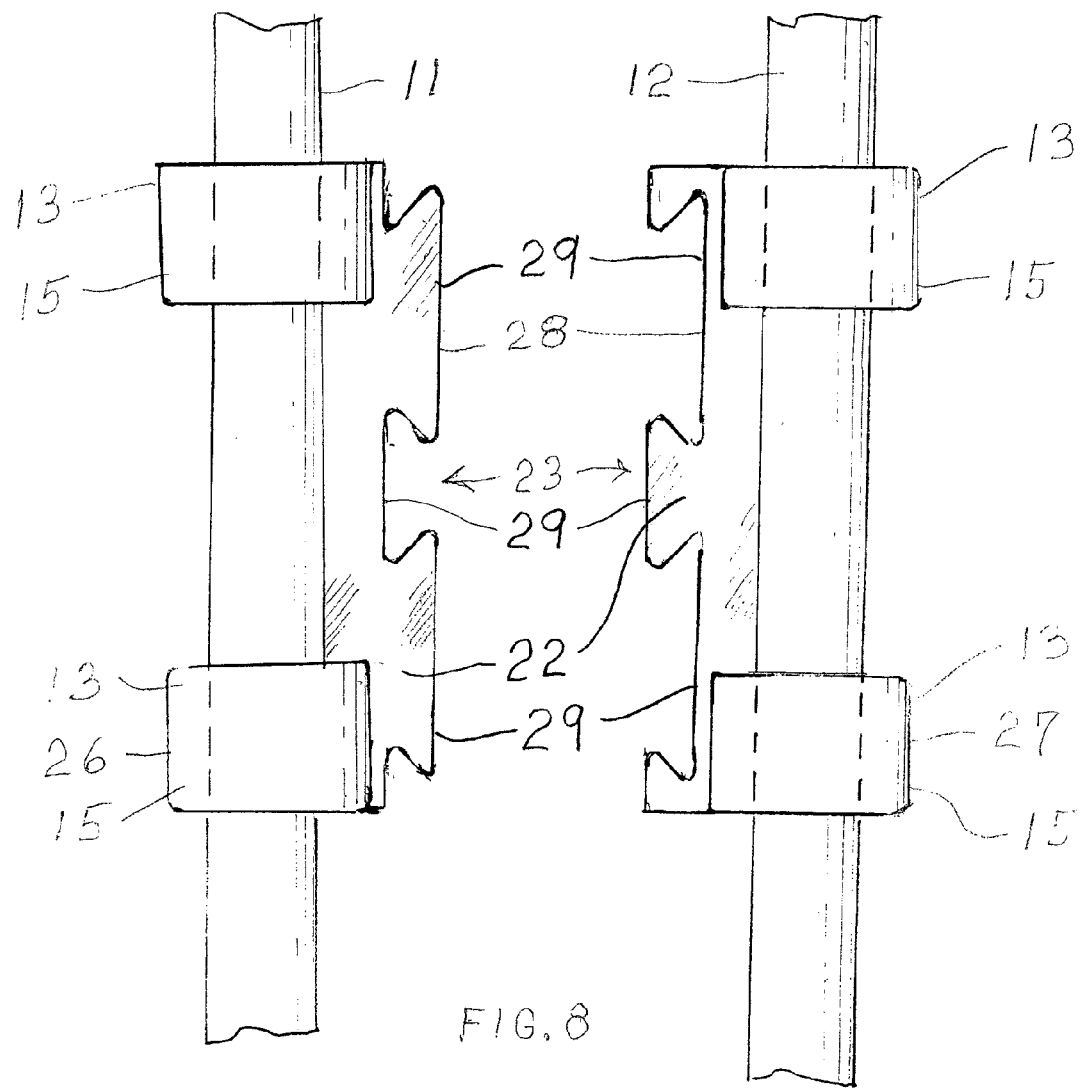

LEAD COUPLER FOR MULTIPLE NEUROLOGICAL STIMULATION LEADS

CROSS REFERENCE

This application claims the benefit of U.S. Provisional Patent Application No. 61/627,166, filed 7 Oct. 2011, entitled Apparatus and Method for a Multipurpose Device Joining Perineural Equipment, the contents of which are incorporated herein by reference.

BACKGROUND OF THE INVENTION

Implantable neurological stimulation systems include a neuro stimulator and an electrical stimulation lead or leads. The implantable neurological stimulation system delivers electrical pulses to tissue, such as neurological tissue or muscle to treat a medical condition.

One such neurological stimulation system is for spinal cord stimulation (SCS) to treat chronic pain. The leads used for SCS are implanted percutaneously through a large needle inserted into the epidural space. The use of dual leads is common and most dual lead systems are implanted as two individual single lead implants. Even if the leads are implanted simultaneously, it is difficult to control the relative position of the two leads with respect to one another. In addition, there is no guarantee that the leads will not migrate or move relative to one another, thereby reducing therapy effectiveness.

There is an industry wide emphasis on maximizing neuromodulation outcomes. The selection of proper neural targets plays a significant role in achieving successful therapies using neuromodulation. Capture of these neural targets with precise electrical energy fields is a significant challenge. The target fibers within the spinal cord are arranged in such a way that is very difficult to access them with just the right amount of electrical energy. Successful neuromodulation requires delivering a balance of energy that reaches the proper neural targets without creating uncomfortable neural stimulation. This balance is particularly difficult to achieve with only one percutaneous neuro stimulator lead due to the lack of electrical field dispersion. This balance is also challenging for neuromodulation equipment that uses "single source" systems of energy. The spatial relationship between the neuromodulation equipment (the lead) and the spinal cord determine the chances of successful capture of target nerve fibers. Generating "central points of stimulation" can be very useful in achieving successful neuromodulation. Each central point of stimulation increases the odds of capturing the target nerve fibers along the spinal cord. If the neural targets along the spinal cord are located between the electrical contact points on the lead, it may be impossible to achieve successful neuromodulation. Creation of central points of stimulation depends upon the technology of the neuromodulation equipment as well as the spinal relationship and orientation of the electrode contact points on the equipment. Thus, there is tremendous benefit to optimize and secure the spatial relationship between the leads in relation to each other as well as in relation to the spinal cord itself.

The position of multiple leads relative to each other cannot be predicted or predetermined, nor maintained. This creates variability in the programming and the pattern of the field of electrical current which is generated. The vertical positioning between electrodes is imperfect as is the horizontal distance between them. both of these factors determine the shape and size of the electrical field which must be generated and optimal positioning is required otherwise programming becomes more difficult and the chances of the treatment benefiting the patient decreases.

Spinal cord stimulation makes use of different types of leads in order to effectively deliver electrical impulses to the spinal cord. These leads come in several shapes and sizes, and each has a pattern or array of electrical contact points, otherwise known as electrodes. The pattern or arrangement of the electrical contact points determine how each lead may be programmed so as to deliver varying electrical impulses. When a single lead is used the vertical arrangement of the electrode array is the primary factor that determines the size and shape of the electrical field which may be generated by opposing charges assigned to specific electrodes along the length of the lead. Leads may be positioned side by side as well. This makes it possible to create fields of current along a horizontal axis in addition to a vertical axis. Thus, the ability to position the spinal stimulator leads beside one another carries significant benefit and it provides a means to increase programming options as pertains to the arrangement of the leads once inserted into a patient. Enhanced programming options will translate into superior patient outcome with their SCS treatment.

As previously indicated, a serious problem encountered is lead migration. A percutaneous style lead is narrow and cylindrical in shape. At present, current devices which facilitate insertion of these leads beneath the skin are only capable of allowing placement of one lead at a time. Once the lead is passed beneath the skin of a patient, it is meant to reside in a specific tissue place or space, typically the epidural space next to the spinal cord. Once within the deep tissue space, because of its size and shape, the lead is highly subject to movement. The movement can occur in a vertical and/or horizontal plane. This problem happens often in the practice of medicine using SCS, and the problem is known as lead migration.

The consequence of lead migration is usually that it results in a significant change in the pattern of electrical signal generated around the spinal cord. This may create pain for a patient or render the previously useful SCS therapy worthless. A surgical revision to reposition the lead is necessary in such cases. Currently, there are anchoring devices available to tie the lead to a fixed point beneath the skin, but these have been shown to be defeatable and lead migration occurs despite their use. Leads with greater size and bulk have been manufactured to address this problem, but add discomfort and risk to the patient. Thus, their existing need to insert percutaneous SCS leads with the result that once they are inserted the possibility of their migration is reduced.

Currently it is not possible to preset or predetermine the arrangement of ones percutaneous SCS array relative to another or a multiple of others. It is also not possible to link these electrode arrays such that their vertical and horizontal inter-spacing is maintained once they are placed into a patient or subject. Furthermore, it is not possible to effectively simultaneously place pairs of multiple SCS electrode arrays into the target tissue space of the patient. A device with such capabilities so as to achieve all these goals is greatly needed.

SUMMARY OF THE INVENTION

The lead coupler of the present invention couples multiple elongated neurological stimulation leads together to form a lead assembly for effectively delivering electrical impulses to subcutaneous tissue for treatment while minimizing migration. The lead coupler of the present invention includes a set of interconnected expandable elastic (such as silicone) lead retainers, preferably collars, one collar for each lead, wherein the collars are dimensioned and contoured for respectively receiving and retaining the leads with an elastic constraint in a predetermined side by side arrangement.

The lead coupler normally includes spaced multiple sets of these collars which engage the multiple leads therealong at spaced intervals. All or at least selected of these spaced multiple collar sets are interconnected with flexible strips which accordingly tie the collar sets together and thereby reduce the potential of lead migration due to the tied series of collar enlargements, and also to provide a path for inclusion of additional conductor leads and sensors for sensing electrical forces around the lead assembly and translating the sense forces to a feedback control for regulating the electrical impulses delivered to the lead assembly. For example, such a sensor may be selected as an accelerometer.

The collars, and/or the flexible connecting strips between collars, may further include electrical stimulation electrodes in order to provide additional possible electrical stimulation capabilities in the lead assembly.

Each side by side set of interconnected collars are preferably interconnected with a releasable connection whereby the lead assembly may be preconfigured as a single or a multiple lead assembly. This releasable connection between the side by side collars may be provided in the form of a snap fit puzzle connection for easy connection or disconnection.

BRIEF DESCRIPTION OF THE DRAWINGS

Other objects and advantages appear hereinafter in the following description and claims. The accompanying drawings show, for the purpose of exemplification, without limiting the scope of the invention or the appended claims, certain practical embodiments of the present invention wherein:

FIG. 7 is an end view illustrating a second embodiment of the implantable neurological stimulation lead assembly of the present invention having a releasable connection between the normally interconnected lead retainers in the form of a snap fit puzzle interfit; and FIG. 8 is a top view of the lead assembly shown in FIG. 7 with the snap fit puzzle interfit connection between lead retainers shown in separated form.

DETAILED DESCRIPTION OF PREFERRED EMBODIMENTS

Figure 1:
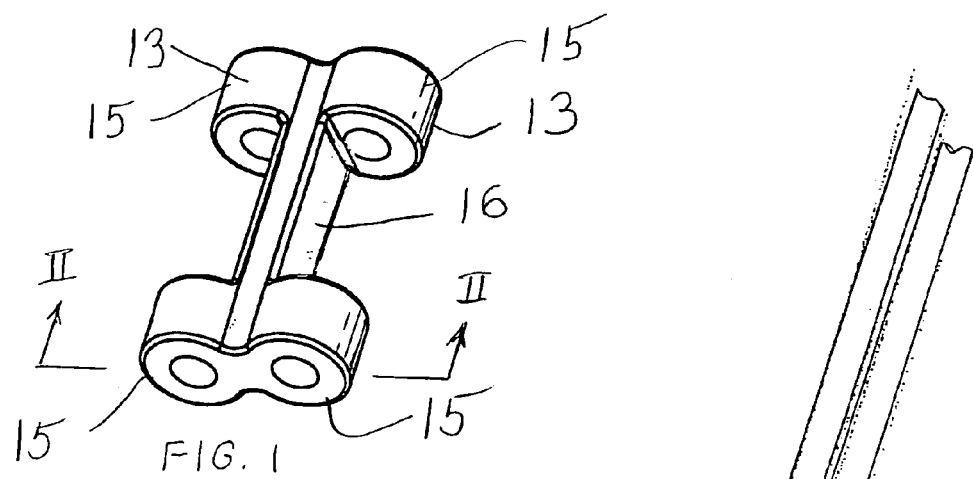
FIG. 1 is an isometric view of one embodiment of the lead coupler of the present invention.
Figure 2:
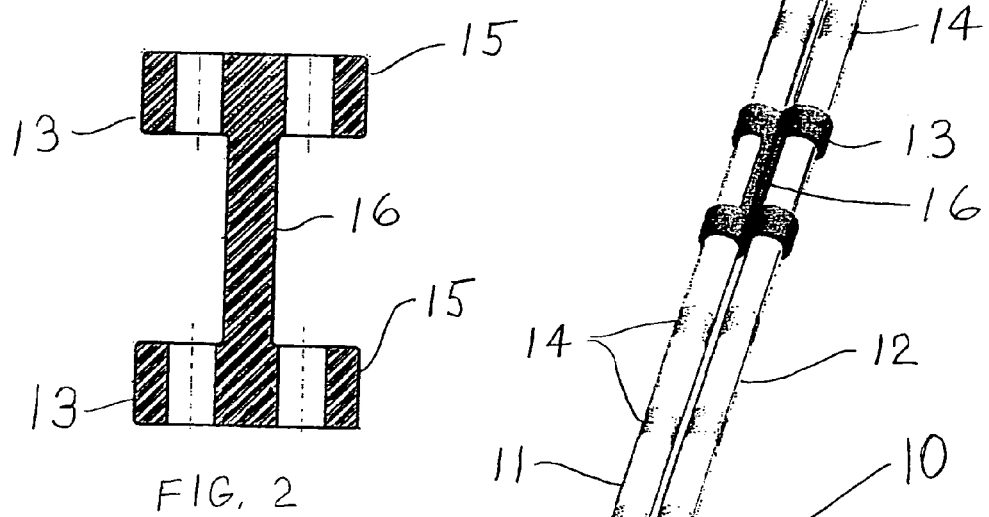
FIG. 2 is a sectional view of the lead coupler shown in FIG. 1 as seen along section line II-II.
Figure 3:
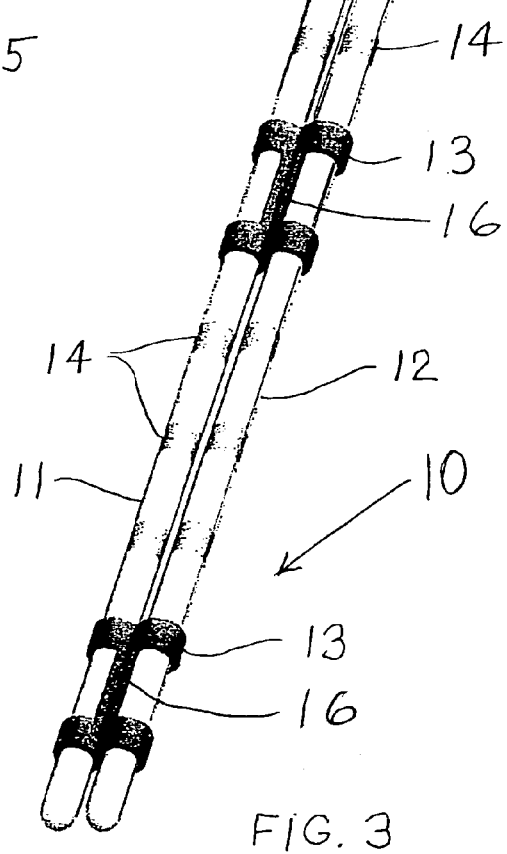
FIG. 3 is an isometric view of an implantable neurological stimulation lead assembly of the present invention incorporating the lead coupler shown in FIG. 1.

Referring to FIGS. 1, 2 and 3, the implantable neurological stimulation lead assembly 10 of the present invention has multiple elongated neurological stimulation leads 11 and 12 coupled together in parallel with lead couplers 13. The leads 11 and 12 include electrodes 14 which deliver electrical pulses to tissue, such as neurological tissue or muscle to treat a medical condition.

The lead couplers 13 include a set of interconnected expandable elastic collars 15, one collar 15 for each lead 11 and 12, whereby the collars 15 respectively receive and retain the leads 11 and 12 with an elastic constraint in a predetermined side by side array as illustrated in FIG. 3. The lead couplers 13 are constructed of an expandable elastic material, such as silicone, which also has the advantage of not being rejected by the human body.

As illustrated in FIG. 3, the lead assembly 10 includes a multiple of the lead couplers 13 longitudinally spaced along and engaging and retaining leads 11 and 12. The lead collar 15 sets are in longitudinally connected to each other as illustrated in FIG. 3 with flexible connecting strips 16.

Figure 4:
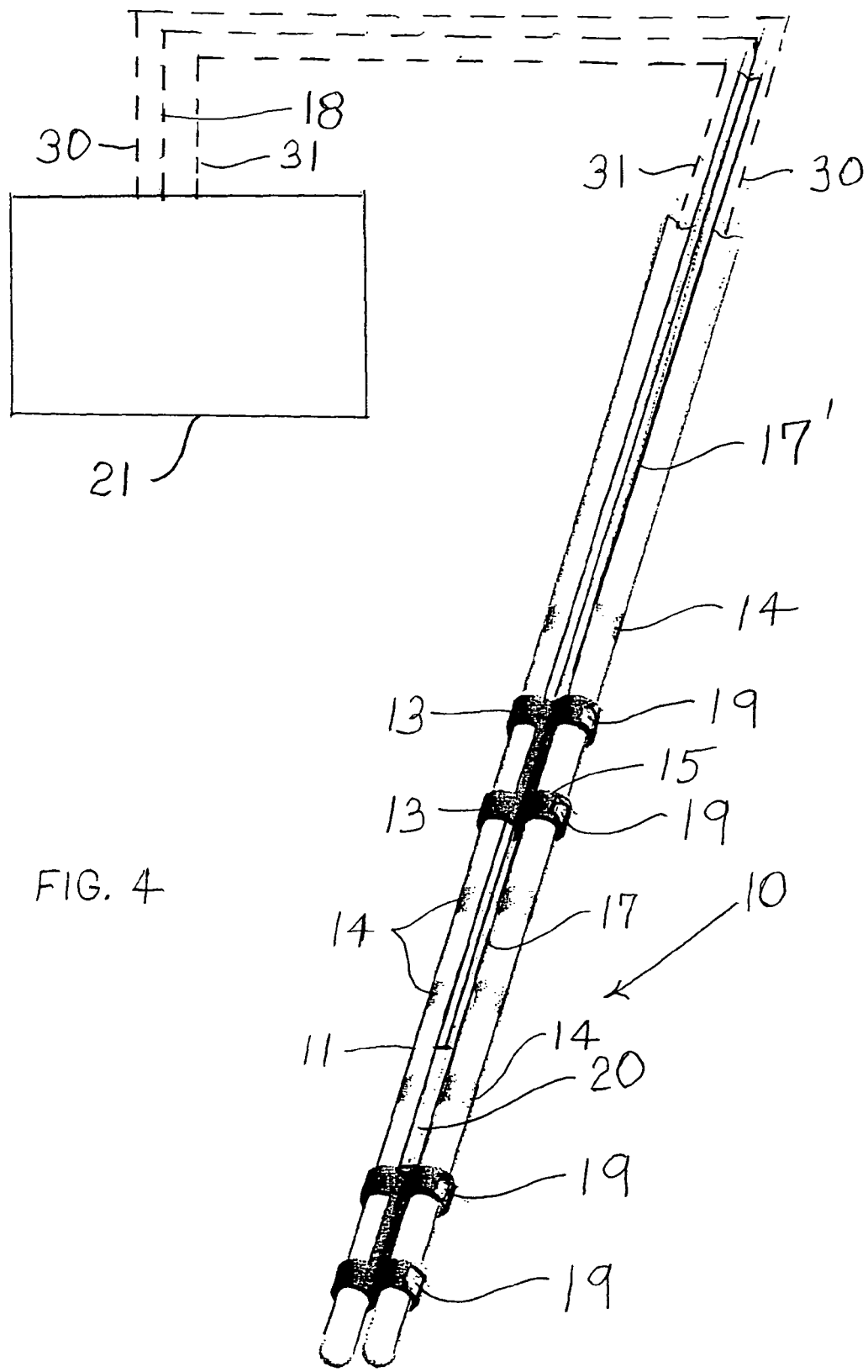
FIG. 4 is an isometric view of another embodiment of the implantable neurological stimulation lead assembly of the present invention shown schematically connected to a central control.

As illustrated in the embodiment of FIG. 4, the lead assembly 10 is illustrated with two longitudinally spaced lead couplers 13 which are further interconnected with elongated flexible connecting strips 17. Flexible connecting strip 17 further continues longitudinally on above the upper set of lead couplers 13 as indicated at 17' and internally carries conductors 18 which supply electrical impulses to additional electrodes 19 provided on the lead couplers 13 to further supplement the stimulation possibilities when combined with the electrodes 14 on leads 11 and 12. Electrodes 14 on leads 11 and 12 are respectively energized from control 21 through conductors 30 and 31. In addition, flexible connection 17 also incorporates a feedback sensor in the form of accelerometer 20. Accelerometer 20 is electrically linked to the central neurological stimulator control 21 through one or more of the electrical conductors 18. Accelerometer 20 permits the lead assembly 10 of the present invention to discern where the lead couplers 13 and those items attached to the lead couplers 13 are in space. This is valuable information as it can be used to control the energy put out to the electrodes in the spinal cord stimulator leads 11 and 12 themselves as it provides a feedback signal to control 21. Control 21 additionally provides neurological stimulation signals as a pulse generator to all electrodes on the lead assembly 10.

The multiple lead couplers 13 are longitudinally spaced along leads 11 and 12 not only to precisely position and maintain the leads 11 and 12 together with their corresponding electrodes 14 in precise side by side alignment in order to secure the optimal spacial relationship between the leads 11 and 12, but they also ensure maintenance of the optimal relationship to the spinal cord of the patient being treated as the interconnected multiple lead couplers 13 secure the assembly 10 from movement or migration once implanted in the epidural space.

Figure 5:
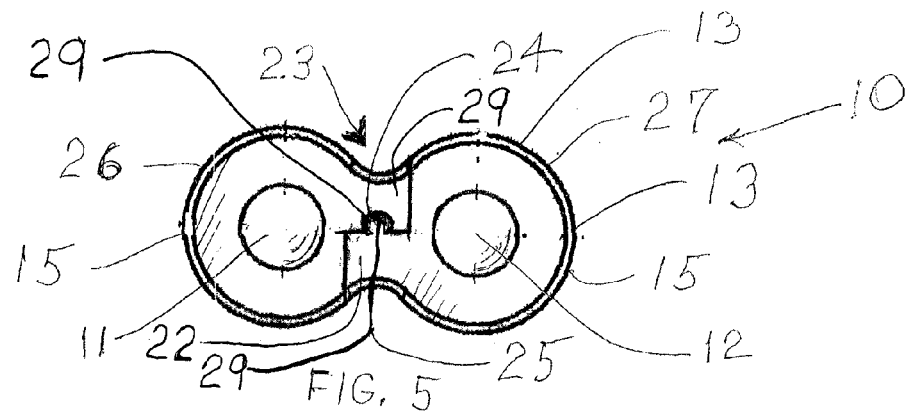
FIG. 5 is an end view illustrating another embodiment of the lead coupler of the present invention retaining two neurological stimulation leads together as a set, the lead coupler having two side by side retaining collars which are interconnected with a releasable connection whereby the lead assembly may be configured as a single or multiple lead assembly.
Figure 6:
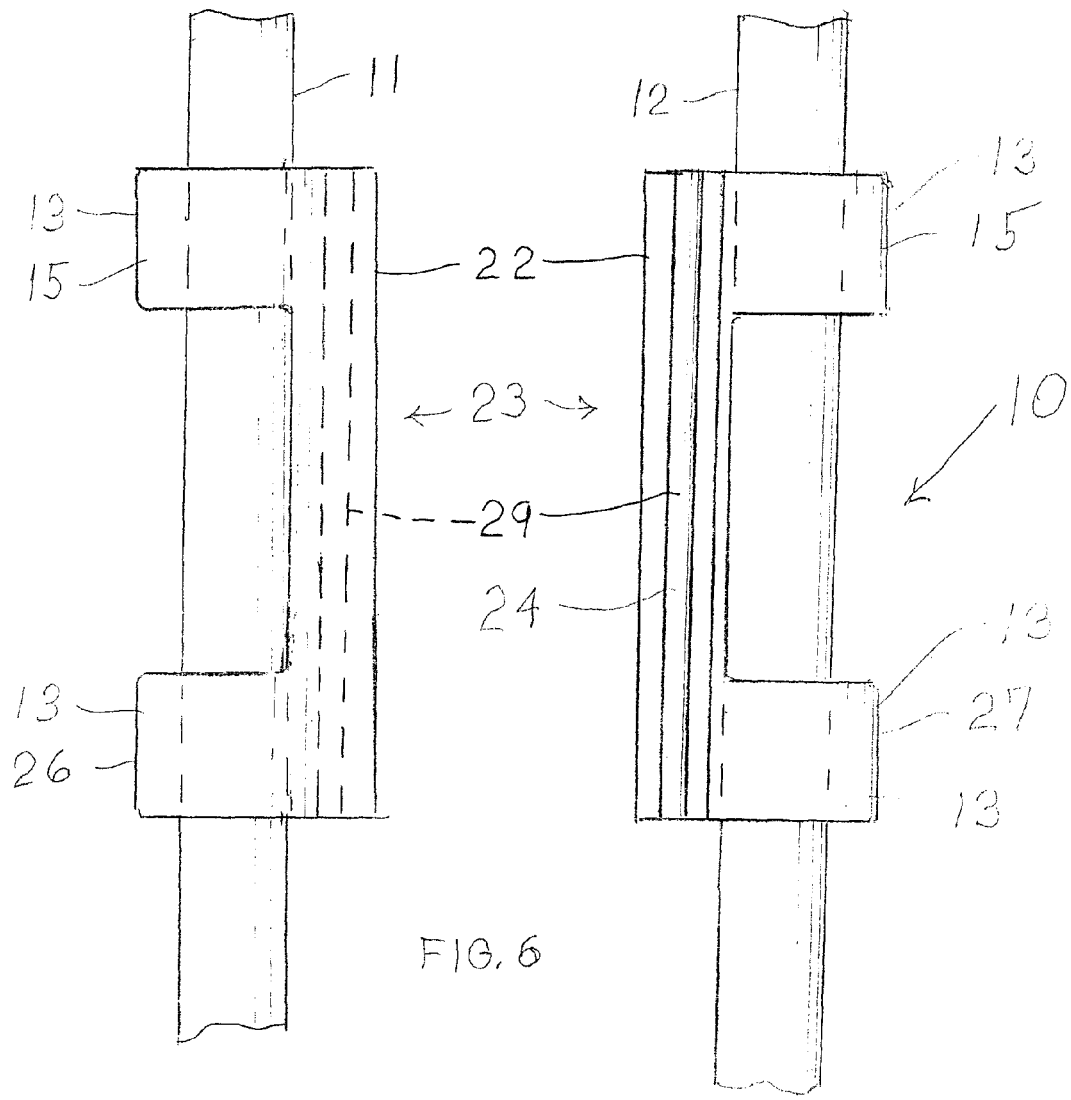
FIG. 6 is a top view of the lead assembly shown in FIG. 5 with the respective lead retainers of the lead coupler separated at the releasable connection therebetween.

Turning next to the embodiment illustrated in FIGS. 5 and 6, the lead coupler 13 there illustrated, as before, includes a set of interconnected lead collars 15 respectively receiving and retaining the leads 11 and 12 with an elastic constraint in a predetermined side by side array as previously illustrated. However, this particular embodiment includes an additional novel feature for the respective lead retainers whereby the side by side collars 15 are interconnected with a releasable connection which is in the form of a snap fit connection. In FIG. 5, the lead retainer in the form of side by side collars 15 are interconnected with the releasable snap fit connection 23 provided in the form of a longitudinal extending and opposing ribs 22 respectively extending laterally from said lead retainer collars 15 toward each other. The ribs 22 have interconnecting connection protrusions 29 in the form of flexible rib protrusion 24 received with a snap fit in the longitudinal coextending and corresponding elastic channel 25, in a fashion similar to the snap fit closure seals that are provided on conventional freezer storage bags. Note that connection protrusions 29 extend transversely in and to ribs 22 to provide a vertically engageable interconnection.

In FIG. 6, the divisable halves 26 and 27 of lead coupler 13 are illustrated in a separated condition. This releasable connection 23 permits the lead assembly 10 to be configured as a single or a multiple lead assembly.

The lead assembly 10 has been illustrated with only two leads 11 and 12, however, the embodiment of FIGS. 5 and 6 may have the features thereof also applied to more than two leads, for example three interconnected leads.

While the enlarged view of FIGS. 5 and 6 appear to provide an assembly 10 which is quite large in size, it should be remembered that the total width of the assembly 10 shown in FIG. 5 is typically no more than approximately 5 mm.

The embodiment of FIGS. 7 and 8 illustrate an alternative flexible snap fit connection 23 from that illustrated in the embodiment of FIGS. 5 and 6. In this embodiment, the lead assembly 10 is in all respects identical to that shown in FIGS. 5 and 6, and therefore similar or identical elements are designated with the same reference numerals. The only difference provided in the assembly 10 of the embodiment shown in FIGS. 7 and 8 is that the flexible snap fit connection 23 provided between lead coupler halves 26 and 27 is that the connection 23 in this embodiment is provided in the form of a puzzle interfit snap connection of 28.

I claim:

1. An implantable neurological stimulation lead assembly having at least one elongate lead connected to a neurological stimulator control for delivering electrical impulses to subcutaneous tissue for treatment;

a lead coupler including at least one lead retainer collar, for each at least one lead, said at least one lead retainer collar respectively receiving and retaining said at least one lead with an elastic constraint whereby said at least one lead retainer collar is moveable relative to said at least one lead to different relative positions therealong for retention under said elastic constraint;

said neurological stimulator control including a feedback control for controlling the energy put out to said lead assembly with a sensed electrical force around said lead assembly as a feedback signal;

said lead coupler including a feedback sensor for sensing said electrical forces around said lead assembly and transmitting the sensed forces to said feedback control for regulating the electrical impulses delivered by said lead assembly whereby said feedback sensor may be positioned and retained relative to said lead assembly by changing the position of said lead coupler relative to said lead assembly under said elastic constraint.

2. The lead assembly of claim 1, wherein said feedback sensor in said lead coupler is an accelerometer for sensing positional forces on said lead assembly and transmitting the sensed forces to said feedback control for regulating the electrical impulses delivered by said lead assembly.

3. A lead coupler for coupling multiple elongated neurological stimulation leads together to form a lead assembly for delivering electrical impulses to subcutaneous tissue for treatment, said lead coupler including;

a set of interconnected lead retainer collars, one for each lead, said lead retainer collars dimensioned and contoured for respectively receiving and retaining said leads with an elastic constraint in a predetermined side by side array;

said set of interconnected lead retainer collars interconnected with a releasable connection comprised of longitudinally extending and opposing ribs respectively extending laterally from said lead retainer collars toward each other, said ribs respectively having interconnecting connection protrusions which extend transversely to said ribs whereby said protrusions are interengagable with each other by axially rotating one of said lead retainer collars into the other for thereby vertically engaging said protrusions of said connection to interconnect said lead retainer collars.

\* \* \* \* \*